US010335323B2

(12) United States Patent
Umebayashi

(10) Patent No.: US 10,335,323 B2
(45) Date of Patent: Jul. 2, 2019

(54) METHOD FOR PRODUCING DISPOSABLE WORN ARTICLE

(71) Applicant: ZUIKO CORPORATION, Osaka (JP)

(72) Inventor: Toyoshi Umebayashi, Osaka (JP)

(73) Assignee: Zuiko Corporation, Osaka (JP)

( * ) Notice: Subject to any disclaimer, the term of this patent is extended or adjusted under 35 U.S.C. 154(b) by 298 days.

(21) Appl. No.: 15/310,165

(22) PCT Filed: Jun. 25, 2015

(86) PCT No.: PCT/JP2015/068375
§ 371 (c)(1),
(2) Date: Nov. 10, 2016

(87) PCT Pub. No.: WO2015/199185
PCT Pub. Date: Dec. 30, 2015

(65) Prior Publication Data
US 2017/0156937 A1    Jun. 8, 2017

(30) Foreign Application Priority Data

Jun. 26, 2014  (JP) .................................. 2014-131023

(51) Int. Cl.
*A61F 13/49*       (2006.01)
*A61F 13/15*       (2006.01)
(Continued)

(52) U.S. Cl.
CPC ........ *A61F 13/15723* (2013.01); *A61F 13/15* (2013.01); *A61F 13/15593* (2013.01);
(Continued)

(58) Field of Classification Search
CPC .......... A61F 13/49011; A61F 13/49012; A61F 13/49061; A61F 13/15699;
(Continued)

(56) References Cited

U.S. PATENT DOCUMENTS

2006/0254708 A1   11/2006  Wada et al.
2013/0255864 A1*  10/2013  Schneider ......... A61F 13/15593
                                                156/161
2015/0328056 A1*  11/2015  Een ..................... A61F 13/15699
                                                604/385.3

FOREIGN PATENT DOCUMENTS

JP      H04-53556       2/1992
JP      2007-181543 A   7/2007
(Continued)

OTHER PUBLICATIONS

Machine English translation of JP2013094420 (Year: 2013).*
(Continued)

*Primary Examiner* — Scott W Dodds
(74) *Attorney, Agent, or Firm* — Renner, Otto, Boisselle & Sklar, LLP

(57) ABSTRACT

A method including the steps of: applying an adhesive on an elastic member extending in a carrying direction; sandwiching the elastic member between two sheets of continuous non-woven fabric having a pair of side edge portions extending in the carrying direction, and bonding together the two sheets of continuous non-woven fabric along parts of a middle portion between the pair of side edge portions via the adhesive applied on the elastic member so that the two sheets of continuous non-woven fabric are laid on each other, thereby producing a continuous member; and thermally welding together the two sheets of continuous non-woven fabric along the pair of side edge portions, which are closer to edges of the continuous member than the middle portion bonded by the adhesive.

3 Claims, 2 Drawing Sheets

(51) Int. Cl.
    *B32B 5/02*     (2006.01)
    *B32B 37/06*     (2006.01)
    *B32B 37/12*     (2006.01)
    *A61F 13/496*     (2006.01)

(52) U.S. Cl.
    CPC ........ *A61F 13/15739* (2013.01); *A61F 13/49* (2013.01); *A61F 13/496* (2013.01); *A61F 13/49011* (2013.01); *B32B 5/022* (2013.01); *B32B 37/06* (2013.01); *B32B 37/12* (2013.01); *B32B 2555/02* (2013.01)

(58) Field of Classification Search
    CPC .. A61F 2013/49025; A61F 2013/49026; A61F 2013/49028
    USPC .............................................. 156/179, 306.6
    See application file for complete search history.

(56) References Cited

FOREIGN PATENT DOCUMENTS

| | | | | | |
|---|---|---|---|---|---|
| JP | 2007181543 | A | * | 7/2007 | |
| JP | 2013094420 | A | * | 5/2013 | ....... A61F 13/49446 |
| WO | WO 2005-013871 | A1 | | 2/2005 | |
| WO | 2013/065619 | A1 | | 5/2013 | |
| WO | WO 2013-148381 | A1 | | 10/2013 | |

OTHER PUBLICATIONS

Extended European Search Report for corresponding European Application No. 15811038.7 dated Nov. 7, 2017.
International Search Report Issued in PCT/JP2015/068375 dated Sep. 15, 2015.

\* cited by examiner

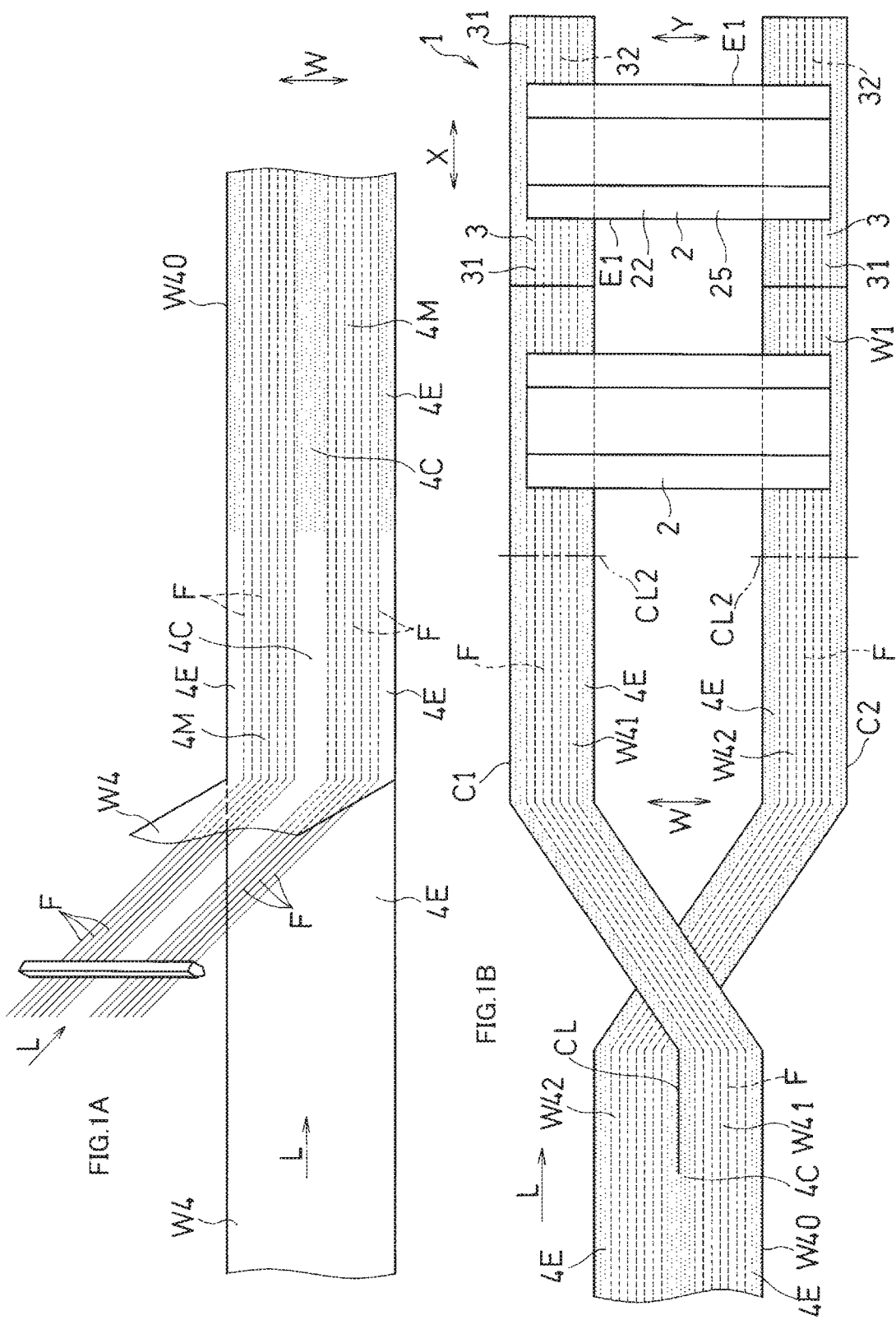

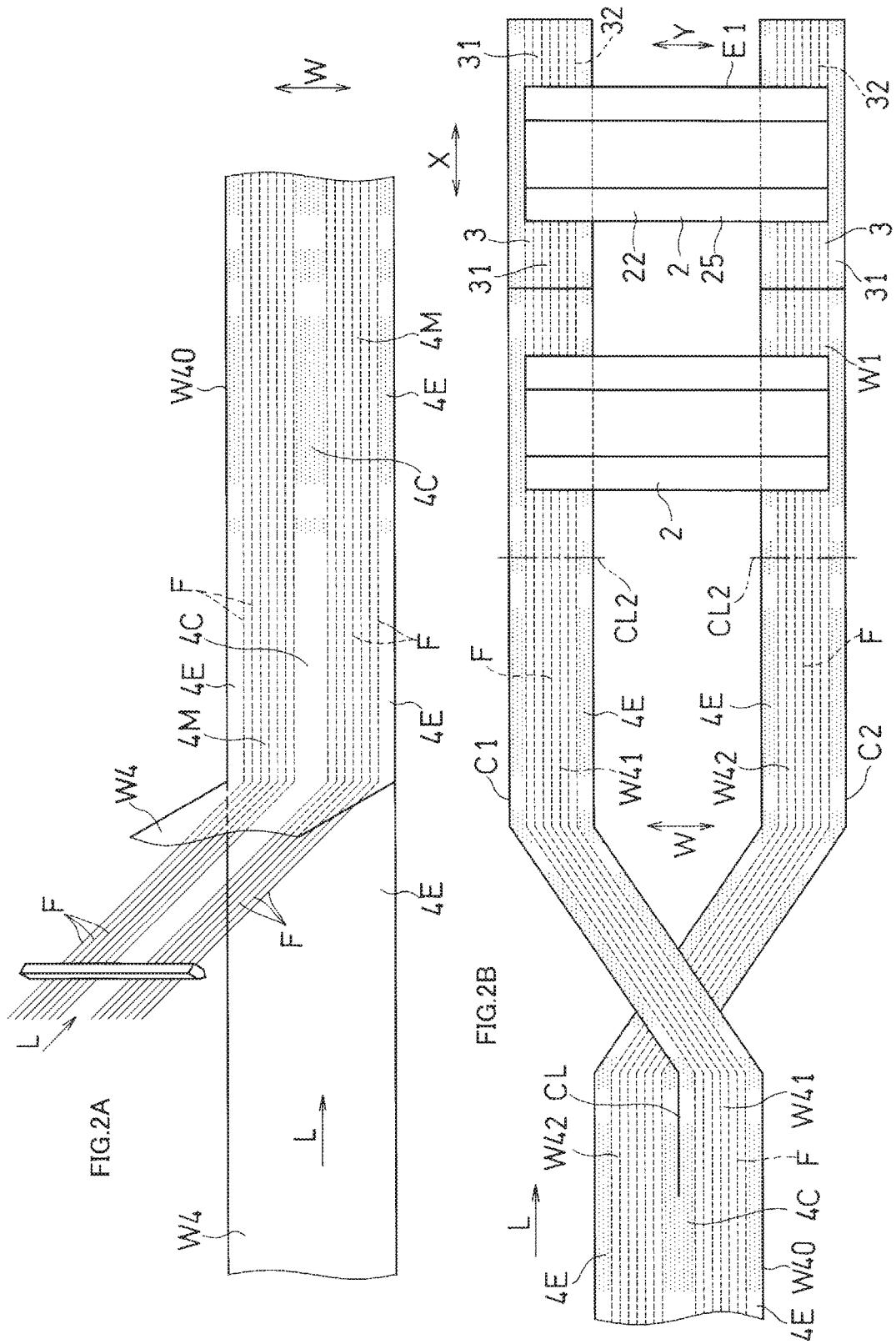

METHOD FOR PRODUCING DISPOSABLE WORN ARTICLE

TECHNICAL FIELD

The present invention relates to a method for producing a disposable worn article.

BACKGROUND ART

A method of sandwiching a continuous elastic member between two sheets of continuous non-woven fabric and bonding the two sheets of continuous non-woven fabric together with an adhesive, thereby producing an around-torso member extending in the girth direction, is well known in the art. If the adhesive is applied up to a pair of side edge portions of the continuous non-woven fabric in the carrying direction, the adhesive may flow (spill) over the continuous non-woven fabric. On the other hand, if no adhesive is applied on the side edge portions of the continuous non-woven fabric, the appearance of the side edge portions deteriorates.

CITATION LIST

Patent Literature

[First Patent Document] WO2005/013871A1
[Second Patent Document] JP2007-181543A

SUMMARY OF INVENTION

In the method for producing a worn article of Document 1 above, an elastic member is sandwiched between two sheets of non-woven fabric, thereby forming an around-torso member that is stretchable in the girth direction. A part, corresponding to a waist part of a wearer, of one non-woven fabric of the around-torso member is folded back, thereby improving the appearance. In such a case, the non-woven fabric in the waist portion is folded back, which requires accordingly more non-woven fabric, resulting in a waste of material.

On the other hand, according to the method for producing a worn article of Document 2 above, the non-woven fabric in the waist portion is not folded back. However, if the two sheets of non-woven fabric are attached also along the opposite edge portions via an adhesive applied on the elastic member in order to improve the breathability in the around-torso area, pleats are formed due to the shrinkage of the elastic member along the opposite edge portions of the around-torso member, thereby deteriorating the appearance.

It is an object of the present invention to provide a method for producing a disposable worn article, with which the material cost can be reduced and some improvement in appearance can be expected.

The present invention is directed to a method including the steps of;
applying an adhesive on an elastic member extending in a carrying direction;
sandwiching the elastic member between two sheets of continuous non-woven fabric having a pair of side edge portions extending in the carrying direction, and bonding (gluing) together the two sheets of continuous non-woven fabric along a part (parts) of a middle (an intermediate) portion between the pair of side edge portions via the adhesive applied on the elastic member so that the two sheets of continuous non-woven fabric are laid on each other, thereby producing a continuous member; and
thermally welding (heat welding) together the two sheets of continuous non-woven fabric along the pair of side edge portions, the side edge portions being closer to edges of the continuous member than the middle portion bonded by the adhesive.

According to the present invention, the two sheets of continuous non-woven fabric are bonded together, with the elastic member sandwiched therebetween, along the middle portion between the pair of side edge portions. On the other hand, the two sheets of continuous non-woven fabric are thermally welded together (by heat welding) along the pair of side edge portions, which are closer to the edges than the middle portion.

Thus, along the side edge portion, which is the upper end of the around-torso member, it is unlikely that pleats are formed due to the shrinkage of the elastic member, thus improving the appearance. Moreover, there is no need to fold back the side edge portions, thereby reducing the material cost.

BRIEF DESCRIPTION OF DRAWINGS

FIG. 1A and FIG. 1B are conceptual diagrams each showing a method for producing a disposable worn article according to Embodiment 1 of the present invention.

FIG. 2A and FIG. 2B are conceptual diagrams each showing Embodiment 2.

DESCRIPTION OF EMBODIMENTS

In a preferred production method, the production step is performed while the two sheets of continuous non-woven fabric are unbonded (not bonded) together along a central region with no adhesive therebetween, wherein the central region extends in the carrying direction and divides the middle portion in two in a width direction perpendicular to the carrying direction;
the thermally welding step is performed while the two sheets of continuous non-woven fabric are thermally welded together also along the central region as well as along the pair of side edge portions; and
the method further includes a step of cutting (slitting) and dividing the continuous member along a virtual cutting (severing) line extending in the carrying direction in the central region into a first divided non-woven fabric and a second divided non-woven fabric.

In this case, the pair of around-torso members is obtained from two sheets of continuous non-woven fabric laid on each other. The two sheets of continuous non-woven fabric are aligned together at the cut (severed) edges along the cutting line of the cut first and second divided non-woven fabrics, and the appearance will be further improved.

A more preferred production method further includes:
changing a positional relationship between the first divided non-woven fabric and the second divided non-woven fabric in the width direction so that the pair of side edge portions are placed between a first cut (severed) edge of the first divided non-woven fabric along the cutting line and a second cut (severed) edge of the second divided non-woven fabric along the cutting line and so that the pair of side edge portions face (oppose to) each other; and
after the changing, placing the absorbent body so that the absorbent body bridges between the first and second divided non-woven fabrics and so that the absorbent body is laid on (overlaps) a portion of the first and second divided non-woven fabrics, while the first and second divided non-woven fabrics are carried generally in parallel to each other in the carrying direction, thereby producing a continuous laminate.

In this case, the cut edges having a good appearance are at the upper end of the around-torso member, and the appearance will be further improved.

Preferably, the thermally welding step is performed by intermittently welding (i.e., there is a pause between weldings) together the two sheets of continuous non-woven fabric along the pair of side edge portions.

Intermittently-welded side edge portions will have a smaller rigidity than a rigidity of continuously-welded side edge portions, and will have an improved wearability.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

A structure of a worn article 1 according to Embodiment 1 of the present invention will now be described with reference to the drawings.

FIG. 1A and FIG. 1B show Embodiment 1.

As shown in FIG. 1B, the worn article 1 of Embodiment 1 has a left-right symmetric shape and structure, and includes an absorbent body 2 and a pair of around-torso members 3. The absorbent body 2 includes a torso portion covering the front torso of the wearer and extending in the girth direction X, a torso portion covering the rear torso of the wearer and extending in the girth direction X, and a crotch portion 22 covering the crotch between these torso portions.

The crotch portion 22 extends in the longitudinal direction Y perpendicular to the girth direction X. The absorbent body 2 forms a part or a whole of the crotch portion 22.

When worn, the crotch portion 22 is folded in two along a line parallel to the girth direction X. Thus, end portions in the girth direction X of one of the pair of around-torso members 3 are laid on those of the other around-torso member 3.

The absorbent body 2 includes an absorbent core (not shown), and this absorbent core absorbs body fluid. The absorbent core is sandwiched between a top sheet and a back sheet, and these sheets and the absorbent core are layered together.

The top sheet is formed by a thin liquid-permeable non-woven fabric and covers the skin-contact surface of the absorbent core. A cuff 25 may be provided on the top sheet.

The back sheet covers the non-skin-contact surface of the absorbent core and is formed by a liquid-impermeable resin sheet. The around-torso members 3 are attached to the end portions of the absorbent body 2 in the longitudinal direction Y.

The around-torso members 3 each protrude from the absorbent body 2 in the girth direction X, and form a part of the front and rear around-torso portions. That is, the around-torso members 3 protrude past the crotch portion 22 in the girth direction X, and extend, in the girth direction X, past the opposite edge portions (the end portions in the girth direction) E1 of the absorbent body 2.

The around-torso members 3 are provided with an elastic member 32 for fitting the worn article 1 to the wearer. The elastic member 32 may be, for example, a plurality of rubber threads, rubber tapes, a material including at least one sheet of film or a thermoplastic resin, or the like.

The elastic member 32 may be nullified (left with no shrinking force) in the center of the torso portion. For example, the elastic member 32 may be nullified in areas where the end portions of the absorbent body 2 in the longitudinal direction Y are laid on the around-torso members 3.

The absorbent body 2 may include around-leg portions necked (constricted, narrowed) in conformity with the legs of the wearer. In the around-leg portions or in areas continuous with the around-leg portions of the around-torso members 3, another elastic member made of rubber threads may be provided, for example, so as to conform around the legs of the wearer.

Where the worn article is a diaper, male touch fasteners (not shown) may be secured to the skin-contact surface of flaps 31 of one around-torso member 3, whereas female touch fasteners may be secured to the non-skin-contact surface of the other around-torso member 3.

Note that a tape material with a fastening agent applied thereon may be used instead of the male touch fasteners, and in this case, the front around-torso member 3, etc., needs to be provided with a surface on which the fastening agent adheres easily.

Where the worn article is pants-shaped, the end portion in the girth direction X of the front around-torso member 3 and that of the rear around-torso member 3 may be welded to each other.

The absorbent body 2 is attached to the skin-contact surface of the around-torso members 3.

In the present specification, the "skin-contact surface" refers to a surface that directly or indirectly faces the skin of the wearer when the worn article 1 is worn, and the "non-skin-contact surface" refers to the surface opposite to the skin-contact surface.

Next, a method for producing the worn article 1 according to Embodiment 1 will be described with reference to FIG. 1A and FIG. 1B.

As shown in FIG. 1A, a plurality of threads of a continuous elastic member F extending in the carrying direction L are carried in the carrying direction L while being stretched in the carrying direction L. An adhesive is applied, continuously in the carrying direction L, on the continuous elastic member F.

After the application of adhesive, the continuous elastic member F is sandwiched between two sheets of continuous non-woven fabric W4 having a pair of side edge portions 4E and extending in the carrying direction L, and the two sheets of continuous non-woven fabric W4 are laid on each other and bonded together via the adhesive applied on the continuous elastic member F, thereby producing a continuous member W40.

The continuous elastic member F is placed continuously along middle portions 4M that exclude the pair of side edge portions 4E of the continuous non-woven fabric W4 and a central region 4C, which is generally in the center area. The central region 4C refers to a band-shaped region that extends in the carrying direction L and divides the middle portion 4M in two in the width direction W perpendicular to the carrying direction L. Specifically, one of the divided middle portions 4M is located between the central region 4C and one side edge portion 4E, and the other divided middle portion 4M is located between the central region 4C and the other side edge portion 4E. In other words, in the width direction W, the central region 4C is sandwiched between the two middle portions 4M.

That is, the continuous member W40 is produced while the two sheets of continuous non-woven fabric W4 are not bonded together via the adhesive along the pair of side edge portions 4E and are not bonded together via the adhesive along the central region 4C.

After the bonding, the two sheets of continuous non-woven fabric W4 are continuously thermally welded together along the pair of side edge portions 4E of the continuous member W40, which are closer to the edges of the continuous member W40 than the middle portions 4M bonded by the adhesive. Simultaneously, in the present embodiment, the two sheets of continuous non-woven fabric W4 are continuously thermally welded together along the central region 4C, in addition to along the pair of side edge portions 4E.

In the figures, the thermally-welded areas are shaded with dots. Note that the welding may be welding using a so-called "ultrasonic energy" or may be welding using a heat seal, or the like.

As shown in FIG. 1B, the continuous member W40 having the pair of side edge portions 4E is slit along a straight cutting line CL while being carried in the carrying direction L.

The continuous member W40 is slit along the central region 4C. By the slitting, the central region 4C is divided in two in the width direction W. Note that the continuous member W40 may be slit so that the continuous member W40 is divided into two equal parts in the width direction W.

Thus, the continuous member W40 is divided into a first divided non-woven fabric W41 and a second divided non-woven fabric W42. The divided non-woven fabrics W41 and W42 each form one around-torso member 3 or the other around-torso member 3.

On the first divided non-woven fabric W41, the continuous elastic member F is placed between one of the slit pieces of the central region 4C and one side edge portion 4E. On the second divided non-woven fabric W42, the continuous elastic member F is placed between the other one of the slit pieces of the central regions 4C and the other side edge portion 4E.

Then, the first divided non-woven fabric W41 and the second divided non-woven fabric W42 of FIG. 1B are moved relative to each other in the width direction W perpendicular to the carrying direction L so that the two divided non-woven fabrics W41 and W42 are separated (spaced apart) from each other in the width direction W.

In the present embodiment, the positional relationship in the width direction W between the first divided non-woven fabric W41 and the second divided non-woven fabric W42 is changed so that the pair of side edge portions 4E are placed between a first cut edge C1 of the first divided non-woven fabric W41 along the cutting line CL and a second cut edge C2 of the second divided non-woven fabric W42 along the cutting line CL and so that the pair of side edges 4E oppose each other.

That is, the positional relationship between the first and second divided non-woven fabrics W41 and W42 is changed so that the first cut edge C1 and the second cut edge C2 are separated from each other in the width direction W and so that the pair of side edge portions 4E are placed between the first and second cut edges C1 and C2. The pair of side edge portions 4E is separated (spaced apart) from each other while opposing each other in the width direction W.

Then, the absorbent body 2 is placed so as to bridge between the first divided non-woven fabric W41 and the second divided non-woven fabric W42 and so as to be laid on a portion of the divided non-woven fabrics W41 and W42, while the first and second divided non-woven fabrics W41 and W42 are carried generally in parallel to each other in the carrying direction L, thereby producing a continuous laminate W1.

Then, the continuous laminate W1 is cut (severed) along a virtual severing line CL2 indicated by a two-dot-chain line to a size (unit) of each individual worn article 1. That is, after the bridging, the around-torso members 3 (the first and second divided non-woven fabrics W41 and W42) are severed in the width direction W between adjacent absorbent bodies 2 to a length that corresponds to the individual worn article 1. Thus, individual worn articles 1 shown in FIG. 1B are obtained.

Note that the continuous laminate W1 may be folded in two while in a continuous state before being cut into the individual worn articles 1. That is, the continuous laminate W1 may be folded in two so that the first and second divided non-woven fabrics W1 and W2 are laid on each other.

Next, another embodiment will be described.

In the following embodiment, different structures and steps from those of Embodiment 1 will be described primarily and similar structures and steps to those of Embodiment 1 will not be described.

FIG. 2A and FIG. 2B show Embodiment 2.

In this embodiment, the step of welding the pair of continuous non-woven fabrics W4 to each other shown in FIG. 2A is performed by intermittently, rather than continuously, welding the two sheets of continuous non-woven fabric W4 along the pair of side edge portions 4E and along the central region 4C.

In the present production method, the continuous elastic member F may also be placed in the central region 4C, and the pair of continuous non-woven fabrics W4 may be bonded together by an adhesive with the continuous elastic member F sandwiched between the continuous non-woven fabrics W4 also in the central region 4C.

The positional relationship between the first and second divided non-woven fabrics W41 and W42 does not need to be changed so that the pair of side edge portions oppose each other, but the absorbent body 2 may be placed therebetween after the distance between the first cut edge C1 and the second cut edge C2 is widened in the width direction W. That is, the first cut edge C1 and the second cut edge C2 may be separated (spaced apart) from each other in the width direction W, and the absorbent body 2 may be placed between the separated first and second cut edges C1 and C2 while the pair of side edge portions are not placed therebetween.

The continuous member W40 does not need to be cut along the straight cutting line CL, but may be cut along a wave-shaped (corrugated) cutting line. The cutting line CL does not always need to divide the continuous member W40 into two equal parts, but may only need to divide the continuous member W40 into two divided non-woven fabrics W41 and W42.

The worn article may be a so-called T-shaped diaper, rather than H-shaped. Also in this case, the around-torso members may be produced from two sheets of continuous non-woven fabric W4, but the dividing step does not need to be performed.

While preferred embodiments have been described above with reference to the drawings, obvious variations and modifications will readily occur to those skilled in the art upon reading the present specification.

For example, the cuff, etc., may be absent (not provided) in a worn article produced by the present production method. Moreover, the tension of the elastic member may be nullified in a part of the area of the around-torso member that overlaps the absorbent body.

Moreover, changing the positional relationship between the first and second divided non-woven fabrics in the width direction may be achieved by flipping over the first and second divided non-woven fabrics.

Thus, such changes and modifications are deemed to fall within the scope of the present invention, which is defined by the appended claims.

INDUSTRIAL APPLICABILITY

The present invention is applicable to pants-type and diaper-type worn articles.

REFERENCE SIGNS LIST

1: Worn article 2: Absorbent body 22: Crotch portion 25: Cuff 3: Around-torso member
31: Flap 32: Elastic member E1: Edge portion F: Continuous elastic member
C1: First cut edge C2: Second cut edge CL: Cutting line CL2: Severing line
W1: Continuous laminate W4: Continuous non-woven fabric 4E: Side edge portion
W40: Continuous member W41,W42: Divided non-woven fabric
L: Carrying direction W: Width direction X: Girth direction y: Longitudinal direction

The invention claimed is:

1. A method for producing a disposable worn article including an around-torso member configured to cover a torso of a wearer and extend in a girth direction and an absorbent body configured to cover a crotch of the wearer, the method comprising the steps of:
applying an adhesive on an elastic member extending in a carrying direction;
sandwiching the elastic member between two sheets of continuous non-woven fabric having a pair of side edge portions extending in the carrying direction, and bonding together the two sheets of continuous non-woven fabric along a part of a middle portion between the pair of side edge portions via the adhesive applied on the elastic member so that the two sheets of continuous non-woven fabric are laid on each other, thereby producing a continuous member; and
thermally welding together the two sheets of continuous non-woven fabric along the pair of side edge portions, which are closer to edges of the continuous member than the middle portion bonded by the adhesive, wherein:
the sandwiching step further comprises forming an unbonded central region without adhesive, the central region extending in the carrying direction and dividing the middle portion in two, and
the thermally welding step further comprises thermally welding the two sheets of continuous non-woven fabric together along the central region,
the method further comprises:
a step of cutting and dividing the continuous member, after the thermally welding step, along a virtual cutting line extending in the carrying direction in the central region into a first divided non-woven fabric and a second divided non-woven fabric;
a step of changing a positional relationship between the first and the second divided non-woven fabrics in a width direction perpendicular to the carrying direction by moving the first and the second divided non-woven fabrics relative to each other in the width direction so that the first and the second divided non-woven fabrics are spaced apart from each other in the width direction;
a step of placing absorbent bodies, after the changing step, so that each of the absorbent bodies bridges between the first and the second divided non-woven fabrics and so that each of the absorbent bodies is laid on a portion of the first divided non-woven fabric and on a portion of the second divided non-woven fabric, while the first and the second divided non-woven fabrics are carried in parallel to each other in the carrying direction, thereby producing a continuous laminate; and
a step of cutting the continuous laminate, after the placing step, in the width direction between the absorbent bodies adjacent to each other so that the continuous laminate is cut into an individual disposable worn article, wherein
the step of changing the positional relationship between the first and the second divided non-woven fabrics is carried out by crossing the first and the second divided non-woven fabrics so that the pair of side edge portions are placed between a first cut edge of the first divided non-woven fabric along the cutting line and a second cut edge of the second divided non-woven fabric along the cutting line, thereby the pair of side edge portions being spaced apart from each other while opposing each other in the width direction.

2. The production method according to claim 1, wherein the thermally welding step is performed by intermittently welding together the two sheets of continuous non-woven fabric along the pair of side edge portions.

3. The production method according to claim 1, wherein the two sheets of continuous non-woven fabric are continuously thermally welded together along the pair of side edge portions of the continuous member; and
the two sheets of continuous non-woven fabric are continuously thermally welded together along the central region.

* * * * *